United States Patent [19]

Burow et al.

[11] Patent Number: 5,164,401

[45] Date of Patent: Nov. 17, 1992

[54] METHOD OF DIURETIC TREATMENT WITH 3,7-DIAZABICYCLO[3,3,1]NONANE COMPOUNDS

[75] Inventors: Kurt Burow; Gerd Buschmann, both of Hanover; Arman Farjam, Wienhausen; Ulrich Kuehl, Gehrden; Gerda Varchmin, Hanover; Deiter Ziegler, Ronnenberg; Uwe Schoen, Burgdorf, all of Fed. Rep. of Germany

[73] Assignee: Kali-Chemie Pharma GmbH, Hanover, Fed. Rep. of Germany

[21] Appl. No.: 714,886

[22] Filed: Jun. 17, 1991

[30] Foreign Application Priority Data

Jun. 15, 1990 [DE] Fed. Rep. of Germany ....... 4019080

[51] Int. Cl.$^5$ ............................................. A61K 31/44
[52] U.S. Cl. ..................................... 514/300; 514/869
[58] Field of Search ................................. 514/300, 869

[56] References Cited

U.S. PATENT DOCUMENTS

| | | | |
|---|---|---|---|
| 3,962,449 | 6/1976 | Binnig et al. | 514/300 |
| 4,183,935 | 1/1980 | Binnig et al. | 514/300 |
| 4,550,112 | 10/1985 | Schoen et al. | 514/278 |
| 4,906,640 | 3/1990 | Schoen et al. | 514/300 |
| 4,912,113 | 3/1990 | Schoen et al. | 514/278 |

FOREIGN PATENT DOCUMENTS 2375235  7/1978  France .

*Primary Examiner*—Leonard Schenkman
*Attorney, Agent, or Firm*—Foley & Lardner

[57] ABSTRACT

A method of treating a mammal in need of diruetic treatment by administering an effective diuretic amount of a diuretically active 3,7,9,9-tetrasubstituted 3,7-diazabicyclo[3,3,1]nonane compound, diuretic pharmaceutical compositions containing an effective diuretic amount of a diuretically active 3,7,9,9-tetrasubstituted 3,7-diazabicyclo[3,3,1]nonane compound; and previously unknown diuretically active 3,7,9,9-tetrasubstituted 3,7-diazabicyclo[3,3,1]nonane compounds containing an optionally substituted phenylalkyl group in the 3-position.

6 Claims, No Drawings

METHOD OF DIURETIC TREATMENT WITH 3,7-DIAZABICYCLO[3,3,1]NONANE COMPOUNDS

BACKGROUND OF THE INVENTION

The present invention relates to the use of 3,7,9, 9-tetrasubstituted 3,7-diazabicyclo[3,3,1]nonane compounds as diuretically active pharmacologically active substances, to diuretically active medicaments which contain 3,7,9,9-tetrasubstituted 3,7-diazabicyclo-[3, 3,1]nonane compounds as active substances, and also to novel 3,7,9,9-tetrasubstituted 3,7-diazabicyclo-[3,3, 1]nonane compounds with valuable pharmacological properties, in particular diuretic effects.

3,7-diazabicyclo[3,3,1]nonane compounds which are 3,7,9,9-tetrasubstituted by aliphatic groups and have properties affecting the heart, in particular anti-arrhythmic properties, are known from EP-A-O 103 833. EP-A-O 306 871 describes 3,7,9,9-tetrasubstituted 3,7-diazabicyclo[3, 3,1]nonane compounds which have in the 3-position an optionally substituted benzhydryl or cinnamyl group and have properties affecting the heart, in particular bradycardic and calcium-antagonistic properties, and have a beneficial effect on the cardiac rhythm. In EP-A-O 301 245, 3,7,9,9-tetrasubstituted 3,7-diazabicyclo[3,3,1]nonane compounds are described which have a benzyl group in the 3-position and serve as intermediate products for the production of 3,7,9, 9-tetrasubstituted 3,7-diazabicyclo[3,3,1]nonane compounds having a substituted sulfonyl group in the 3-position which have pharmacological effects affecting stomach motility.

SUMMARY OF THE INVENTION

It is the object of the invention to provide a new method of treating humans and other mammals in need of diuretic treatment.

Another object of the invention is to provide new diuretic pharmaceutical compositions having an improved activity profile.

A further object of the invention is to provide new 3,7-diazabicyclo[3,3,1]nonane compounds which exhibit diuretic activity.

The objects of the invention are achieved according to a first aspect of the invention by providing a method of diuretic treatment of a mammal, said method comprising administering to a mammal in need of diuretic treatment, a diuretically effective amount of a 3,7-diazabicyclo[3,3, 1]nonane compound corresponding to the Formula I:

wherein
R$^1$ represents an alkyl group containing from 1 to 6 carbon atoms, an alkylene group containing from 3 to 6 carbon atoms having a double bond which is not linked directly to the nitrogen atom, a cycloalkylalkyl group containing from 4 to 9 carbon atoms, or a benzyl group,
R$^2$ represents a lower alkyl group, and
R$^3$ represents a lower alkyl group, or
R$^2$ and R$^3$ together form an alkylene chain containing from 3 to 6 carbon atoms, and
R$^4$ represents an alkyl group containing from 1 to 6 carbon atoms, an alkenyl group containing from 3 to 6 carbon atoms having a double bond which is not linked directly to the nitrogen atom, a cycloalkylalkyl group containing from 4 to 9 carbon atoms, a group corresponding to the Formula a:

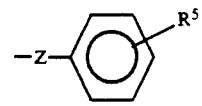

wherein
R$^5$ represents hydrogen, halogen, lower alkyl or lower alkoxy, and
Z represents an alkylene chain containing from 1 to 3 carbon atoms or a propenylene chain having a double bond which is conjugated with the phenyl group, or
a group corresponding to the Formula b:

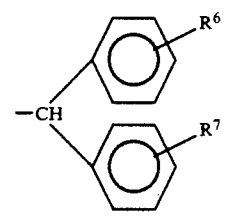

wherein
R$^6$ represents hydrogen, halogen, lower alkyl or lower alkoxy, and
R$^7$ represents hydrogen, halogen, lower alkyl or lower alkoxy,
or a physiologically acceptable acid addition salt thereof.

According to a further aspect of the invention, the objects are achieved by providing a diuretic pharmaceutical composition comprising an effective diuretic amount of at least one diuretically active 3,7-diazabicyclo[3,3,1]nonane compound corresponding to the formula I:

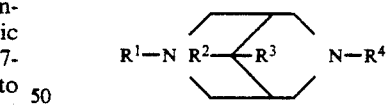

wherein
R$^1$ represents an alkyl group containing from 1 to 6 carbon atoms, an alkylene group containing from 3 to 6 carbon atoms having a double bond which is not linked directly to the nitrogen atom, a cycloalkylalkyl group containing from 4 to 9 carbon atoms, or a benzyl group,
R$^2$ represents a lower alkyl group, and
R$^3$ represents a lower alkyl group, or
R$^2$ and R$^3$ together form an alkylene chain containing from 3 to 6 carbon atoms, and
R$^4$ represents an alkyl group containing from 1 to 6 carbon atoms, an alkenyl group containing from 3 to 6 carbon atoms having a double bond which is not linked directly to the nitrogen atom, a cycloalkylalkyl group containing from 4 to 9 carbon atoms, a group corresponding to the Formula a:

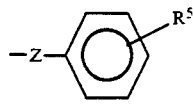

wherein $R^5$ represents hydrogen, halogen, lower alkyl or lower alkoxy, and

Z represents an alkylene chain containing from 1 to 3 carbon atoms or a propenylene chain having a double bond which is conjugated to the phenyl group, or a group corresponding to the Formula b:

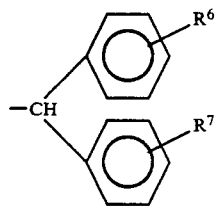

wherein $R^6$ represents hydrogen, halogen, lower alkyl or lower alkoxy, and $R^7$ represents hydrogen, halogen, lower alkyl or lower alkoxy, or a physiologically compatible acid addition salt thereof, and at least one conventional pharmaceutical adjuvant, carrier or diluent.

In yet another aspect of the invention, the objects are achieved by providing a 3,7-diazabicyclo[3,3,1]nonane compound corresponding to the Formula Ia:

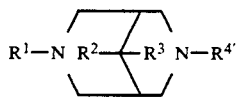

wherein $R^1$ represents an alkyl group containing from 1 to 6 carbon atoms, an alkenyl group containing from 3 to 6 carbon atoms having a double bond which is not linked directly to the nitrogen atom, a cycloalkylalkyl group containing from 4 to 9 carbon atoms, or a benzyl group, $R^2$ represents a lower alkyl group, and $R^3$ represents a lower alkyl group, or $R^2$ and $R^3$ together form an alkylene chain containing from 3 to 6 carbon atoms, and $R^{4'}$ represents a group corresponding to the Formula a':

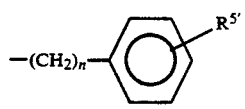

wherein n represents an integer from 1 to 3, and $R^{5'}$ represents halogen, a lower alkyl group, a lower alkoxy group, or if n is 2 or 3, $R^{5'}$ may also be hydrogen, or a pharmaceutically acceptable acid addition salt thereof.

DETAILED DESCRIPTION OF PREFERRED EMBODIMENTS

According to the invention, 3,7-diazabicyclo[3,3,1]nonane compounds corresponding to the formula I:

wherein $R^1$ is an alkyl group with 1-6 carbon atoms, an alkylene group with 3-6 carbon atoms having a double bond which is not linked directly to the nitrogen atom, a cycloalkylalkyl group with 4-9 carbon atoms or benzyl, $R^2$ is lower alkyl, and $R^3$ is lower alkyl, or $R^2$ and $R^3$ together form an alkylene chain with 3-6 carbon atoms, and $R^4$ is an alkyl group with 1-6 carbon atoms, an alkenyl group with 3-6 carbon atoms having a double bond which is not linked directly to the nitrogen atom, or a cycloalkylalkyl group with 4-9 carbon atoms, or $R^4$ is a group corresponding to the Formula a:

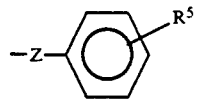

wherein $R^5$ is hydrogen, halogen, lower alkyl or lower alkoxy, and

Z is an alkylene chain with 1-3 carbon atoms or a propenylene chain having a double bond which is conjugated with the phenyl group, or $R^4$ is a group corresponding to the formula b:

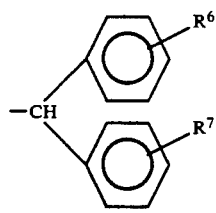

wherein $R^6$ is hydrogen, halogen, lower alkyl or lower alkoxy, and $R^7$ is hydrogen, halogen, lower alkyl or lower alkoxy, or a physiologically compatible acid addition salt thereof is used as the active ingredient in the preparation of a diuretically active pharmacological preparation.

If in the compounds of Formula I, $R^1$ represents an alkyl group, this may be straight-chain or branched and contain from 1 to 6, preferably from 3 to 6, carbon atoms. An alkenyl group $R^1$ may likewise be straight-chain or branched and contain up to 6, preferably 3 or 4, carbon atoms. A cycloalkylalkyl group $R^1$ may contain from 4 to 9, preferably from 4 to 7, carbon atoms and may consist in particular of an alkylene chain containing from 1 to 3 carbon atoms substituted by a cycloalkyl group containing from 3 to 6 carbon atoms, preferably a cycloalkyl-substituted methylene group. Alkyl groups, particularly branched alkyl groups, and cycloalkylmethyl groups have proved especially suitable as groups $R^1$.

If the substituents $R^2$ and $R^3$ represent lower alkyl, these alkyl groups may be straight-chain or branched and contain from 1 to 4, preferably from 1 to 3, carbon atoms. The alkyl groups $R^2$ and $R^3$ are advantageously the same. If $R^2$ and $R^3$ together form an alkylene chain, this may contain from 3 to 6, preferably 4 or 5, carbon atoms.

If in the compounds of Formula I the group $R^4$ represents an alkyl group, it may be a straight-chain or branched alkyl group and contain from 1 to 6, preferably from 3 to 6, carbon atoms. An alkenyl group $R^4$ may be straight-chain or branched and contain up to 6, preferably 3 or 4, carbon atoms. A cycloalkylalkyl group $R^4$ may contain from 4 to 9, preferably 4 to 7, carbon atoms, and represents in particular an alkylene chain with from 1 to 3 carbon atoms substituted by a cycloalkyl group containing from 3 to 6 carbon atoms, preferably a cycloalkyl-substituted methylene group. Alkyl groups, particularly branched alkyl groups, and cycloalkylmethyl groups have proved to be particularly suitable as groups $R^4$.

In the compounds of Formula I, the group $R^4$ may also represent an optionally substituted phenylalkyl or cinnamyl group corresponding to the Formula a. If the substituent $R^5$ on the phenyl group represents or contains lower alkyl, this may contain from 1 to 4, in particular 1 or 2, carbon atoms. A halogen substituent $R^5$ preferably represents fluorine or chlorine. The chain Z may contain from 1 to 3 carbon atoms and represents in particular a methylene group or a propenylene chain having a double bond which is conjugated with the phenyl group.

In the compounds of Formula I, the group $R^4$ may also represent an optionally substituted benzhydryl group b. If the substituents $R^6$ and/or $R^7$ of the benzhydryl group b represent or contain lower alkyl groups, these may contain from 1 to 4, in particular 1 or 2, carbon atoms. Preferred halogen substituents are fluorine or chlorine.

Salts with inorganic acids, e.g. sulfuric acid or hydrohalic acids, especially hydrochloric acid; or with organic acids, for instance lower aliphatic monocarboxylic or dicarboxylic acids such as acetic acid, fumaric acid, tartaric acid, lactic acid, maleic acid, citric acid or salicylic acid; or with sulfonic acids, for instance lower alkyl sulfonic acids such as methane sulfonic acid, or benzene sulfonic acids optionally substituted in the benzene ring by halogen or lower alkyl, such as p-toluene sulfonic acid, are suitable as physiologically acceptable acid addition salts of the compounds of Formula I.

The invention relates to the use of the compounds of Formula I as diuretically active pharmacologically active substances for producing medicaments and to diuretically active medicaments produced using these active substances.

3,7-diazabicyclo[3,3,1]nonane compounds corresponding to the Formula Ia:

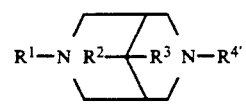

wherein
$R^1$, $R^2$ and $R^3$ have the above meanings and $R^{4'}$ is a group of the Formula a':

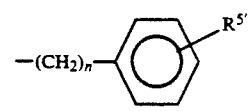

in which n represents an integer from 1 to 3, and $R^{5'}$ represents halogen, lower alkyl, lower alkoxy or, if n is 2 or 3, hydrogen, have not been described in the literature and represent valuable new pharmacologically active substances which are also part of the present invention.

The other compounds of Formula I used as diuretically active substances fall within the scope of the compounds described in the aforementioned European Patent Application Nos. EP 103, 883; EP 301,245; and EP 306,871, and are known from these documents.

Surprisingly, it has been found that the 3,7,9, 9-tetra-substituted 3,7-diazabicyclo[3,3,1]nonane compounds corresponding to Formula I are distinguished by a new type of activity profile and also possess a marked diuretic effect in addition to the aforementioned heart-affecting properties. The compounds used according to the invention are further distinguished by good physiological acceptability and a favorable ratio between sodium and potassium elimination. The diuretic effect of the compounds of Formula I can be demonstrated in pharmacological tests in vivo on animals such as rats.

DESCRIPTION OF PHARMACOLOGICAL TEST METHODS

1. Diuresis Determination on Conscious Rats

The increase in diuresis induced by the test substances was determined on conscious rats. Groups of three animals each were administered the test substances in aqueous solution or suspension per os. In addition, the animals of the test groups and animals of a control group were each administered a quantity of 25 ml per kg body weight water per os. Then the urine was collected over 6 hours. The quantity of sodium eliminated in the urine was determined and calculated in milliequivalents per 100 g of body weight. The ratio of the quantity eliminated by the groups of test animals to the quantity eliminated by the group of control animals is listed as an indicator of the increase in diuresis caused by the test substance.

The test results obtained with a representative group of compounds of Formula I according to the method described above are listed in the following Table I:

TABLE I

| No. | R$^1$ | R$^2$ | R$^3$ | R$^4$ | Salt | Dose mg/kg p.o. | Increase in diuresis by factor of |
|---|---|---|---|---|---|---|---|
| 1 | n-C$_6$H$_{13}$— | CH$_3$— | CH$_3$— | n-C$_6$H$_{13}$— | a | 20 | 1.8 |
| 2 | n-C$_3$H$_7$— | C$_2$H$_5$— | C$_2$H$_5$— | n-C$_3$H$_7$— | a | 20 | 8.2 |
| 3 | (CH$_3$)$_2$—CH— | n-C$_3$H$_7$— | n-C$_3$H$_7$— | (CH$_3$)$_2$—CH— | a | 20 | 18.8 |
| 4 | cycloprop-CH$_2$— | —(CH$_2$)$_4$— | | cycloprop-CH$_2$— | a | 20 | 9.8 |
| 5 | n-C$_4$H$_9$— | CH$_3$— | C$_2$H$_5$— | n-C$_4$H$_9$— | a | 20 | 4.9 |
| 6 | cyclohex-CH$_2$— | CH$_3$— | C$_2$H$_5$— | cyclohex-CH$_2$— | a | 20 | 8.8 |
| 7 | n-C$_4$H$_9$— | CH$_3$— | CH$_3$— | (CH$_3$)$_2$—CH—CH$_2$— | a | 20 | 5.0 |
| 8 | n-C$_4$H$_9$— | —(CH$_2$)$_3$— | | n-C$_4$H$_9$— | a | 20 | 3.7 |
| 9 | CH$_2$=CH—CH$_2$—CH$_2$— | —(CH$_2$)$_5$— | | CH$_2$=CH—CH$_2$—CH$_2$— | c | 20 | 10.4 |
| 10 | CH$_2$=CH—CH$_2$—CH$_2$— | CH$_3$— | CH$_3$— | CH$_2$=CH—CH$_2$—CH$_2$— | c | 20 | 4.7 |
| 11 | (CH$_3$)$_2$—CH—CH$_2$— | n-C$_3$H$_7$— | n-C$_3$H$_7$— | CH$_2$=CH—CH$_2$—CH$_2$— | c | 20 | 6.3 |
| 12 | n-C$_4$H$_9$— | CH$_3$— | CH$_3$— | CH$_2$=CH—CH$_2$—CH$_2$— | c | 20 | 9.0 |
| 13 | (CH$_3$)$_2$—CH— | (CH$_2$)$_5$— | | (CH$_3$)$_2$—CH—CH$_2$— | a | 20 | 2.1 |
| 14 | phen-CH$_2$— | CH$_3$— | CH$_3$— | phen-CH$_2$— | d | 10 | 4.3 |
| 15 | n-C$_4$H$_9$— | CH$_3$— | CH$_3$— | phen-CH$_2$— | c | 2.5 | 3.0 |
| 16 | n-C$_4$H$_9$— | CH$_3$— | CH$_3$— | 3-Cl-phen-CH$_2$— | c | 5 | 2.2 |
| 17 | n-C$_4$—H$_9$— | CH$_3$— | CH$_3$— | 2-Cl-phen-CH$_2$— | c | 5 | 3.7 |
| 18 | n-C$_4$—H$_9$— | CH$_3$— | CH$_3$— | 4-CH$_3$O-phen-CH$_2$— | c | 5 | 5.6 |
| 19 | n-C$_4$H$_9$— | CH$_3$— | CH$_3$— | 2,5-di-CH$_3$-phen-CH$_2$— | c | 10 | 2.7 |
| 20 | n-C$_4$H$_9$— | CH$_3$— | CH$_3$— | 4-CH$_3$-phen-CH$_2$— | c | 10 | 2.7 |
| 21 | phen-CH$_2$— | —(CH$_2$)$_4$— | | phen-CH$_2$— | e | 20 | 2.8 |
| 22 | cycloprop-CH$_2$ | —(CH$_2$)$_4$— | | phen-CH$_2$— | a | 20 | 2.4 |
| 23 | cyclohex-CH$_2$— | —(CH$_2$)$_4$— | | phen-CH$_2$— | a | 20 | 2.4 |
| 24 | (CH$_3$)$_2$—CH— | CH$_3$— | CH$_3$— | phen-CH$_2$— | a | 20 | 2.4 |
| 25 | n-C$_4$H$_9$— | CH$_3$— | CH$_3$— | phen-CH=CH—CH$_2$— | b | 10 | 3.8 |
| 26 | (CH$_3$)$_2$—CH—CH$_2$— | CH$_3$— | CH$_3$— | phen-CH=CH—CH$_2$— | a | 20 | 4.0 |
|  |  |  |  |  |  | 10 | 2.2 |
| 27 | cycloprop-CH$_2$— | CH$_3$— | CH$_3$— | phen-CH=CH—CH$_2$— | a | 20 | 2.2 |
| 28 | (CH$_3$)$_2$—CH—CH$_2$— | —(CH$_2$)$_4$— | | phen-CH=CH—CH$_2$— | a | 20 | 2.2 |
| 29 | (CH$_3$)$_2$—CH—CH$_2$— | CH$_3$— | CH$_3$— | 4-F,4'-F-diphe- | a | 1 | 2.1 |
| 30 | n-C$_4$H$_9$— | CH$_3$— | CH$_3$— | 4-F,4'-F-diphe- | a | 20 | 4.6 |
|  |  |  |  |  |  | 2.5 | 2.7 |
| 31 | (CH$_3$)$_2$—CH— | —(CH$_2$)$_4$— | | diphe- | a | 20 | 3.9 |
|  |  |  |  |  | a | 2.5 | 2.2 |
| 32 | (CH$_3$)$_2$—CH— | —(CH$_2$)$_4$— | | 4-F,4'-F-diphe- | a | 20 | 3.4 |
|  |  |  |  |  |  | 5 | 2.2 |
| 33 | cyclohex-CH$_2$— | CH$_3$— | CH$_3$— | diphe- | a | 5 | 2.6 |
| 34 | (CH$_3$)$_2$—CH—CH$_2$— | —(CH$_2$)$_4$— | | diphe- | a | 5 | 2.5 |
| 35 | cycloprop-CH$_2$— | —(CH$_2$)$_4$— | | diphe- | a | 20 | 6.2 |
|  |  |  |  |  |  | 2.5 | 2.8 |
| 36 | phen-CH$_2$— | —(CH$_2$)$_4$— | | diphe- | a | 20 | 4.7 |
|  |  |  |  |  |  | 10 | 4.2 |
| 37 | phen-CH$_2$— | —(CH$_2$)$_4$— | | 4-F,4'-F-diphe- | a | 20 | 5.7 |
|  |  |  |  |  |  | 5 | 3.1 |
| 38 | n-C$_4$H$_9$— | CH$_3$— | CH$_3$— | diphe- | a | 2.5 | 3.0 |
| 39 | cycloprop-CH$_2$— | CH$_3$— | CH$_3$— | diphe- | b | 2.5 | 3.6 |
| 40 | cycloprop-CH$_2$— | CH$_3$— | CH$_3$— | 4-F,4'-F-diphe- | a | 20 | 5.9 |
|  |  |  |  |  |  | 2.5 | 2.1 | cycloprop = Cyclopropyl
phen = Phenyl
cyclohex = Cyclohexyl
diphe = Diphenylmethyl
a = Dihydrogentartrate
b = Monohydrogentartrate
c = Monosalicylate
d = Monohydrogenfumarate
e = Dihydrochloride 2. Determination of Diuretic, Sodium-uretic and Potassium-uretic Effects on Anesthetized Rats The experiments were performed on male Wistar rats having body weights of 320–370 g. The animals were kept without food for approximately 17 hours before the start of the experiments, but had continuous free access to normal tap water.

All the animals were anesthetized by an intraperitoneal injection of urethane (1.3 g/kg) and were then tracheotomized. For intravenous injection of test substances and for infusion of physiological saline solution (6 ml/h), a plastic tube was tied into the left femoral vein. In order to record the arterial blood pressure, the left femoral artery was cannulated. The bladder was exposed by an abdominal incision and was catheterized. The catheter was fixed in the bladder so that the major part of the bladder was functionally disconnected. Then the urethra was ligatured. During preparation, and for the duration of the experiments, the animals lay on a heated operating table. The body temperature was kept at a constant 37° C. In a 5-minute pre-test phase, the urine was collected and the quantities of potassium and sodium eliminated therein were determined. Then the test substances were administered intravenously. The urine eliminated under the action of the test substances was collected for 12 minutes, and the quantities of sodium and potassium eliminated therein were determined. The following Table II shows the values for test substances Nos. 4 and 13 obtained using the test method described above for a dose of 10 μmole/kg.

TABLE II

| Diuretic Action | Test Substance No. | |
| --- | --- | --- |
| | 4[e] | 13[f] |
| Urine elimination in mg/100 g body weight/min | | |
| premliminary phase control value | 1.22 | 1.09 |
| test value | 22.72 | 8.07 |
| Na+ elimination in μmole/100 g body weight/min | | |
| preliminary phase control value | 0.07 | 0.07 |
| test value | 3.47 | 1.53 |
| K+ elimination in μmole/100 g body weight/min | | |
| preliminary phase control value | 0.11 | 0.09 |
| test value | 1.02 | 0.64 |

[e] dihydrochloride
[f] dihydrogen fumarate

It can be seen from the above pharmacological test results that the compounds of Formula I have a marked diuretic effect. It is clear from Table II that in the diuresis brought about by the compounds the sodium elimination increases much more than the potassium elimination. This points to a diuretic effect of the compounds with a physiologically advantageous sodium/potassium elimination profile. Due to their good diuretic properties, the substances are suitable as diuretics for treating conditions in which increased elimination of urine and increased elimination of salt is necessary for the reduction of oedemas.

The beneficial combination of diuretic effectiveness with heart affecting properties exhibited by the substances of Formula I makes them particularly suitable for increasing diuresis and reducing oedemas in the treatment of cardiac failure and hypertonia. The doses to be used may vary individually and will naturally vary according to the type of condition to be treated, the substance used, and the manner of administration. For instance, parenteral formulations will generally contain less active substance than oral preparations. In general, however, pharmaceutical forms containing from 0.5 to 50 mg, in particular from 1 to 20 mg, of active substance per individual dose are suitable for administration to humans and larger mammals.

The compounds may be contained according to the invention, together with conventional pharmaceutical adjuvants and/or carriers, in solid or liquid pharmaceutical preparations. Examples of solid preparations include preparations which can be administered orally, such as tablets, capsules, powders, granules or dragees, or alternatively suppositories. Solid preparations may contain conventional pharmaceutical inorganic and/or organic carriers, e.g. talcum, lactose or starch, in addition to conventional pharmaceutical adjuvants, for instance lubricants or tablet disintegrating agents. Liquid preparations such as solutions, suspensions or emulsions may contain the usual diluents such as water, oils and/or suspending agents such as polyethylene glycols and the like. Other adjuvants may also be added, such as preservatives, taste correctives and the like.

The active substances may be mixed with the pharmaceutical adjuvants and/or carriers and formulated in known manner. In order to produce solid medicament forms, the active substances may for instance be mixed with the adjuvants and/or carriers in a conventional manner and may be granulated in the wet or dry state. Depending on the type of additives used, optionally a powder which can be made into tablets can also be obtained by simple mixing. The granules or powder may be filled directly into capsules or be pressed into tablet cores in the conventional manner. These may then be made into dragees in a known manner, if desired.

The compounds of Formula I may be prepared in a known manner, for instance using the methods described in the European Patent Applications cited above or in a manner analogous to these methods.

For example, compounds of Formula I can be obtained by a) reacting a compound corresponding to the Formula II:

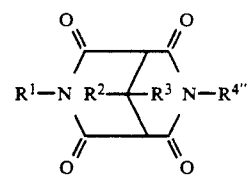

wherein
  $R^1$, $R^2$ and $R^3$ have the above meanings, with a compound corresponding to the Formula III:

$R^4-X$   III wherein
  $R^4$ has the above meaning and
  X represents an aminolytically cleavable group, or b) reducing a compound corresponding to the Formula IV:

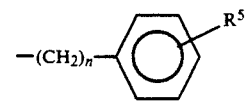

wherein
  $R^1$, $R^2$ and $R^3$ have the above meanings, and
  $R^{4''}$ is an alkyl group with from 1 to 6 carbon atoms, a cycloalkylalkyl group with from 4 to 9 carbon atoms, or a group corresponding to the Formula a'':

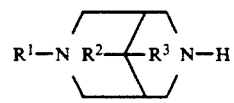

wherein n and $R^5$ have the above meanings, to produce a compound corresponding to the Formula Ib:

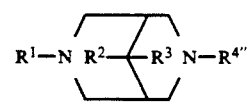

wherein $R^1$, $R^2$, $R^3$ and $R^{4''}$ have the above meanings, and optionally converting a free base compound of Formula I into a physiologically acceptable acid addition salt thereof or converting an acid addition salt into the corresponding free base compound of Formula I.

The reaction of the compounds of Formula II with compounds of Formula III may be carried out in a known manner under standard conditions for alkylating amines. Thus the reaction advantageously is carried out under basic conditions in an organic solvent which is inert under the reaction conditions. Preferably halogens such as chlorine or bromine, or also organic sulfonic acid groups, for instance, radicals of lower alkane sulfonic acids such as methane sulfonic acid or of aromatic sulfonic acids such as benzene sulfonic acids or lower alkyl- or halogen-substituted benzene sulfonic acids, e.g. toluene sulfonic acid or bromobenzene sulfonic acid, are considered to be aminolytically cleavable groups in the compounds of Formula III. In particular, aprotic solvents such as ethers, particularly cyclic ethers such as tetrahydrofuran, dimethyl formamide or aromatic hydrocarbons, are suitable as inert organic solvents. Advantageously, the reaction is carried out in the presence of at least an equivalent quantity of a base. Examples of suitable bases include alkali metal carbonates, alkali metal amides, alkali metal hydrides or lithium organic compounds such as lower alkyl lithium or phenyl lithium. Thus, for example, the use of lithium amide in tetrahydrofuran or dimethyl formamide has proved satisfactory. The reaction temperature may vary according to the type of base used, and be selected between 0° C. and the boiling temperature of the solvent.

The reduction of the tetraoxo compounds of Formula IV may take place using known methods, for instance using complex metal hydrides as reducing agents. For instance, lithium aluminum hydride is highly suitable as a reducing agent. Advantageously, the reduction is carried out in an organic solvent which is inert under the reaction conditions, for instance a cyclic ether such as tetrahydrofuran or a mixture of a cyclic ether and an aromatic hydrocarbon such as toluene, using an excess of the reducing agent at elevated temperature, for instance at temperatures between 80° and 120° C.

The compounds of Formula I may be isolated from the reaction mixture and purified in known manner. Acid addition salts may be converted in conventional manner into the free bases and these bases may, if desired, be converted into pharmacologically acceptable acid addition salts in a known manner.

The starting compounds of Formula II are known and can be produced using known methods, for instance by reduction of compounds of Formula V:

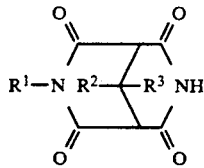

V wherein $R^1$, $R^2$ and $R^3$ have the above meanings. Compounds of Formula IV are known, or can be obtained in known manner, for instance by reacting compounds of Formula V with compounds of Formula IIIb:

$$R^{4''}-X \qquad \text{IIIb}$$

wherein $R^{4''}$ and X have the above meanings.

The following examples are intended to explain the invention in greater detail, but without restricting its scope in any way.

The following Examples 1 to 3 describe pharmaceutical preparations according to the invention which contain an active substance of Formula I, and also the production of such pharmaceutical preparations.

Example 1: Tablets

| Composition: | |
|---|---|
| N,N'-dicyclopropylmethyl-9,9-tetramethylen-3,7-diazabicyclo[3,3,1]nonane dihydrochloride | 20 parts |
| Corn starch | 30 parts |
| Lactose | 55 parts |
| Polyvinylpyrrolidone | 5 parts |
| Magnesium stearate | 2 parts |
| Talcum | 3 parts |
| Total | 115 parts |

PREPARATION METHOD

The active substance was mixed with corn starch and finely powdered lactose in a mixer. The resulting mixture was thoroughly moistened with a 20% solution of polyvinylpyrrolidone ("Kollidon 25", from BASF) in deionized water. If necessary, additional deionized water was added. The moist granules were passed through a 2 mm sieve, dried on trays at 40° C. and then passed through a 1 mm sieve (Frewitt machine). After the granules had been mixed with magnesium stearate and talcum, tablets weighing 115 mg were pressed therefrom, so that each tablet contained 20 mg of the active substance.

Example 2: Capsules

| Composition: | |
|---|---|
| N-isobutyl-N'-isopropyl-9,9-pentamethylen-3,7-diazabicyclo[3,3,1]nonane dihydrogen fumarate | 20 parts |
| Corn starch | 20 parts |
| Lactose | 45 parts |
| Polyvinylpyrrolidone | 3 parts |
| Magnesium stearate | 1.5 parts |
| Highly dispersed silicic acid | 0.5 parts |
| Total | 90 parts |

PREPARATION METHOD

The active substance was mixed with corn starch and finely powdered lactose in a mixer. The resulting mixture was thoroughly moistened with a 20% solution of polyvinylpyrrolidone ("Kollidon 25", from BASF) in deionized water. If necessary, deionized water was added. The moist granules were passed through a 1.6 mm sieve (Frewitt machine), dried on trays at 40° C., and then passed through a 1 mm sieve (Frewitt). After the granules had been mixed with magnesium stearate and highly dispersed silicic acid ("Aerosil 200", from Degussa), 90 mg thereof in each case were filled by means of an automatic encapsulating machine into size 4 hard gelatin capsules, so that each capsule contained 20 mg of active substance.

Example 3: Ampoules

| Composition (per ampoule): | |
|---|---|
| N,N'-dicyclopropylmethyl-9,9-tetramethylen-3,7-diazabicyclo[3,3,1]nonane dihydrochloride | 5 mg |
| Sodium chloride | 16 mg |
| Water for injection purposes to make up to | 2.0 ml |

PREPARATION METHOD

Sodium chloride was dissolved in water for injection purposes. The active substance was added and dissolved while stirring. Sufficient water for injection purposes was added to make up the final volume. The mixture was passed through a 0.25 μ membrane filter. 2.15 ml aliquots were filled into brown glass ampoules, and the ampoules were hermetically closed. The ampoules were sterilized with steam for 30 minutes at 121° C. 2 ml of the resulting injection solution contains 5 mg of the active substance.

The following examples are intended to illustrate the preparation of the compounds of Formula I in greater detail.

EXAMPLE 4

3-butyl-7-(2,5-dimethylbenzyl)-9, 9-dimethyl-3,7-diazabicyclo[3,3,1]nonane=test substance No. 19.

3.5 g 3-n-butyl-9,9-dimethyl-3, 7-diazabicyclo[3,3,1-]nonane were dissolved in 25 ml of dimethyl formamide, and 0.8 g of lithium amide was added to the solution. The reaction mixture was then maintained at a temperature of 60° C. for 1 hour and subsequently allowed to cool. After cooling, a solution of 5.6 g of 2,5-dimethylbenzyl chloride in 10 ml of dimethyl formamide was added dropwise, and the reaction mixture was stirred for a further 4 hours at 80° C. Then aqueous citric acid solution was added to the reaction mixture in order to dissolve the title compound as a citric acid salt. The solution was washed with diethyl ether and then rendered alkaline by adding dilute sodium hydroxide solution, whereupon the title compound was again freed as a base. The free base was extracted with diethyl ether. After the ether extract was dried over magnesium sulfate, the ether solution was filtered, and the ether was distilled off. The remaining oil was purified by distillation in a bulb tube at 210° C. and 0.01 Torr.

The title compound, which was obtained as an oil, was dissolved in ether. A solution of an equimolar quantity of salicylic acid was added dropwise to the solution with stirring and ice cooling. The precipitated salicylate salt was filtered out and dried. 2.1 g of the salicylate salt of the title compound were obtained having a melting point of 153-155° C.

EXAMPLE 5

3-butyl-7-(2,5-dimethylbenzyl)-9, 9-dimethyl-3,7-diazabicyclo[3,3,1]nonane=test substance No. 19.

A) 2.6 g of 3-butyl-9,9-dimethyl-2,4,6, 8-tetraoxo-3,7-diazabicyclo[3,3,1]nonane were heated to 120° C. in 50 ml of dimethyl formamide with 1.7 g potassium carbonate for one hour. After cooling, a solution of 1.8 g of 2,5-dimethylbenzyl chloride in 20 ml of dimethyl formamide was added dropwise to the reaction mixture, and the reaction mixture was heated to 120° C. for another 3 hours. The reaction mixture was worked up by distilling off the dimethyl formamide, taking up the residue in dichloromethane, and washing with water adjusted to an alkaline pH value. The dichloromethane phase was separated, dried over magnesium sulfate, and concentrated. After recrystallizing the remaining crude product residue from ether/acetone, 1.2 g of 3-butyl-7-(2,5-dimethylbenzyl)-9, 9-dimethyl-2,4,6,8-tetraoxo-3,7diazabicyclo[3,3, 1]nonane was obtained having a melting point of 159-161° C.

B) 5 g of lithium aluminum hydride in a mixture of 140 ml of absolute tetrahydrofuran and 60 ml of absolute toluene were heated in an oil bath at a bath temperature of 80° C. At this oil bath temperature, a solution of 11.2 g of 3-butyl-7-(2,5-dimethylbenzyl)-9, 9-dimethyl-2,4,6,8-tetraoxo-3,7-diazabicyclo[3,3, 1]nonane in a mixture of 70 ml of tetrahydrofuran and 30 ml of toluene was added slowly in drops. The reaction mixture was held at a temperature of 120° C. for a further 6 hours. For working up, hydrolysis was then performed under basic conditions by adding 5 ml of water, 5 ml of 15% aqueous sodium hydroxide solution and another 15 ml of water in succession to the reaction mixture. The resulting deposit was filtered out. The filtrate was extracted several times with dichloromethane. The united dichloromethane extracts were dried over magnesium sulfate and concentrated. The remaining oil was purified by distillation in a bulb tube at 210° C. and 0.01 Torr. The resulting oily title compound was reacted with salicylic acid to form the monosalicylate salt, as described in Example 4. The yield was 6.8 g of the salicylate salt of the title compound having a melting point of 153-155° C.

The following compounds of Formula I were also obtained using the methods described in Examples 4 and 5. The test substance numbers relate to Table I above.

| Test Subst. No. | $R^1$ | $R^2$ | $R^3$ | $R^4 =$ $R^{5'}$-phen-$CH_2$— $R^{5'} =$ | Melting point of the monosalicylate in °C. |
|---|---|---|---|---|---|
| 16 | n-$C_4H_9$— | $CH_3$— | $CH_3$— | 3-Cl | 136–139 |
| 17 | n-$C_4H_9$— | $CH_3$— | $CH_3$— | 2-Cl | 146–147 |
| 18 | n-$C_4H_9$— | $CH_3$— | $CH_3$— | 4-$CH_3O$— | 91–95 |
| 20 | n-$C_4H_9$— | $CH_3$— | $CH_3$— | 4-$CH_3$— | 158–160 |

The foregoing description and examples have been set forth merely to illustrate the invention and are not intended to be limiting. Since modifications of the described embodiments incorporating the spirit and substance of the invention may occur to persons skilled in the art, the scope of the invention should be construed to include all variations falling within the ambit of the appended claims and equivalents thereof.

What is claimed is:

1. A method of diuretic treatment of a mammal, said method comprising administering to a mammal in need of diuretic treatment, a diuretically effective amount of a 3,7-diazabicyclo[3,3,1]nonane compound corresponding to the Formula I:

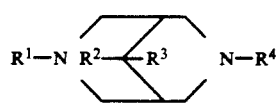

wherein $R^1$ represents an alkyl group containing from 1 to 6 carbon atoms, an alkylene group containing from 3 to 6 carbon atoms having a double bond which is not linked directly to the nitrogen atom, a cycloalkylalkyl group containing from 4 to 9 carbon atoms, or a benzyl group, $R^2$ represents a lower alkyl group, and
$R^3$ represents a lower alkyl group, or
$R^2$ and $R^3$ together form an alkylene chain containing from 3 to 6 carbon atoms, and
$R^4$ represents an alkyl group containing from 1 to 6 carbon atoms, an alkenyl group containing from 3 to 6 carbon atoms having a double bond which is not linked directly to the nitrogen atom, a cycloalkylalkyl group containing from 4 to 9 carbon atoms, a group corresponding to the Formula a:

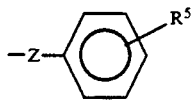

wherein
$R^5$ represents hydrogen, halogen, lower alkyl or lower alkoxy, and
Z represents an alkylene chain containing from 1 to 3 carbon atoms or a propenylene chain having a double bond which is conjugated with the phenyl group, or
a group corresponding to the Formula b:

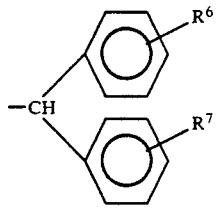

wherein
$R^6$ represents hydrogen, halogen, lower alkyl or lower alkoxy, and
$R^7$ represents hydrogen, halogen, lower alkyl or lower alkoxy,
or a physiologically acceptable acid addition salt thereof.

2. A method according to claim 1, wherein $R^1$ represents an alkyl group containing from 1 to 6 carbon atoms or a cycloalkylalkyl group containing from 4 to 7 carbon atoms.

3. A method according to claim 1, wherein $R^4$ represents an alkyl group containing from 1 to 6 carbon atoms, a cycloalkylalkyl group containing from 4 to 7 carbon atoms, or a group corresponding to Formula b.

4. A method according to claim 1, wherein $R^1$ represents an alkyl group containing from 3 to 6 carbon atoms or a cycloalkylalkyl group containing from 4 to 7 carbon atoms, and $R^4$ represents an alkyl group containing from 3 to 6 carbon atoms or a cycloalkylalkyl group containing from 4 to 7 carbon atoms.

5. A method according to claim 1, wherein said 3,7-diazabicyclo[3,3,1]nonane compound is selected from the group consisting of N,N'-dicyclopropylmethyl-9,9-tetramethylen-3,7-diazabicyclo[3,3,1]nonane, N-isobutyl-N'-isopropyl-9,9-pentamethylen-3, 7-diazabicyclo[3,3,1]nonane, and physiologically acceptable acid addition salts thereof.

6. A method according to claim 1, wherein $R^4$ represents a group corresponding to the formula a':

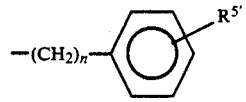

wherein
n represents an integer from 1 to 3, and
$R^{5'}$ represents halogen, a lower alkyl group, a lower alkoxy group, or if n is 2 or 3, $R^{5'}$ may also be hydrogen.

* * * * *